United States Patent [19]

Papavizas

[11] Patent Number: 4,489,161
[45] Date of Patent: Dec. 18, 1984

[54] **STRAIN OF *TRICHODERMA VIRIDE* TO CONTROL FUSARIUM WILT**

[75] Inventor: George C. Papavizas, Beltsville, Md.

[73] Assignee: The United States of America as represented by the Secretary of Agriculture, Washington, D.C.

[21] Appl. No.: 436,497

[22] Filed: Oct. 25, 1982

[51] Int. Cl.$^3$ .................. C12N 1/14; C12R 1/885; C12R 1/77; A61K 37/00
[52] U.S. Cl. .................. 435/254; 435/945; 435/929; 435/911; 424/93
[58] Field of Search ............... 424/93, 195; 435/911, 435/929, 254, 253, 172.1, 945, 911; 414/58

[56] References Cited

PUBLICATIONS

Papavizas, G. C. et al., (including J. A. Lewis and T. H. Abd-El Moity) *Phytopathology* V. 72, pp. 126–132, Jan. 1982.
G. C. Papavizas, Abstract, "Induced Tolerance of Trichoderma harzianum to Fungicides" Phytopathology 70, No. 7, 1980, pp. 691–692.
J. L. Troutman et al., "Induced Tolerance of *T. viride* to Benomyl" Phytopathology News 12, 131, 1978, Abstract #18.
G. C. Papavizas, Abstract, "New Types of *T. viride* with Tolerance to MBC Fungicides," Phytopathology 71, 898, 1981, Aug. 1981.

*Primary Examiner*—Lionel M. Shapiro
*Assistant Examiner*—Robin Teskin
*Attorney, Agent, or Firm*—M. Howard Silverstein; William E. Scott; David G. McConnell

[57] ABSTRACT

A new strain of the fungus *Trichoderma viride* designated as T-1-R9 is described. The new strain is an effective biocontrol agent for fusarium wilt of chrysanthemum.

2 Claims, No Drawings

STRAIN OF *TRICHODERMA VIRIDE* TO CONTROL FUSARIUM WILT

BACKGROUND OF THE INVENTION

1. Field of the Invention

This invention relates to the development of a new biotype of the soilborne beneficial fungus *Trichoderma viride* and more particularly to the ability of the new biotype to tolerate a systemic fungicide and to suppress Fusarium wilt of chrysanthemum.

2. Description of the Art

The development of new strains or biotypes of *Trichoderma viride* resistant to benomyl, a commercially available fungicide, by gamma irradiation has been reported, but the biological control capabilities of the benomyl tolerant biotypes were not described. The development of new biotypes of *Trichoderma harzianum* tolerant to some commercially available fungicides has been described as was the development of ten biotypes of *Trichoderma viride* by ultraviolet radiation. However, the new biotype, T-1-R9, of this invention and its tolerance to fungicides of the methyl benzimidazole carbamate group and its ability to control wilt of chrysanthemums caused by *Fusarium oxysporum* f. sp. *chrysanthemi* has not been described heretofore.

SUMMARY OF THE INVENTION

An object of this invention is to provide a new biotype of the soilborne beneficial fungus *Trichoderma viride*.

Another object is to provide an organism that can tolerate a systemic fungicide.

Still another object is to provide a microorganism that is useful for biological control of a plant disease.

A further object is to provide an organism for controlling Fusarium wilt of chrysanthemum.

A still further object is to provide a method of controlling the wilt of chrysanthemums caused by *Fusarium oxysporum* f. sp. *chrysanthemi*.

According to this invention the above objects are accomplished by a new biotype or strain of the fungus *Trichoderma viride* designated as T-1-P9 and the application of the new biotype to control fusarium wilt of chrysanthemum.

A viable culture of the new strain of the fungus *Trichoderma viride* designated as T-1-R9 has been deposited with the Culture Collection at the Northern Regional Research Center, U.S. Department of Agriculture, Peoria, Ill., 61604, and its accession number is NRRL 15165. With reference to 886 O.G. 638, progeny of this strain will be available during pendency of the patent application to one determined by the Commissioner of Patents and Trademarks to be entitled thereto under 37 CFR 1.14 and 35 USC 122. All restrictions on the availability of progeny of the strain to the public will be irrevocably removed upon the granting of the patent of which the strain is the subject. The new strain produces abundant conidia and chlamydospores, is tolerant to fungicides of the methyl benzimidazole carbamate group, and has the ability to suppress and control the wilt of chrysanthemums caused by *Fusarium oxysporum* f. sp. *chrysanthemi*.

DESCRIPTION OF THE INVENTION

Although the concept of biological control of plant diseases has been known for a number of years, the idea of improving biological control agents by mutagenesis and genetic alteration is relatively new. In fact, the new biotype, T-1-R9, is the first microorganism produced by genetic alteration to be used for biological control of plant disease. T-1-R9 is also the first biological control agent in the Trichoderma genus which combines biological control ability with tolerance to commercially used fungicides such as 1-(butylcarbamoyl)-2-benzimidazole carbamate (benomyl, 50% wettable powder), 2(4-thiazolyl) benzimidazole (thiabendazole, 42.28%F), and dimethyl [(1,2-phenylene) bis (iminocarbonothioyl)]=bis [carbamate] (thiophanate methyl, 70% wettable powder).

The new biotype of this invention, T-1-R9, was produced from strain T-1 of *Trichoderma viride* Pers, ex S.F. Gray. Conidia of T-1 were produced by growing the isolate on V-8 juice agar (200 ml V-8 juice, 800 ml water, 1 g glucose, 15 g agar, 6.0 ml 1.0 N NaOH) for 7 days under continuous fluorescent light (700 $\mu$Ein/m$^2$/sec). Any suitable medium including the commercially used aqueous molasses solution with corn steep liquor can be substituted whenever, in the specification, it is stated that V-8 juice agar has been used. Conidia were removed from the agar surface by pipetting 5 ml of sterile distilled water on the surface and gently rubbing the surface with a sterile cotton-tipped applicator. Conidia were counted in a hemacytometer, and the suspensions were adjusted with water to provide the desired concentration of conidia in each test.

There were five replications in all experiments, and each experiment was done twice. A randomized complete block design was used in all experiments.

The induction and isolation of mutants was accomplished by the following procedure. One-ml aliquots of a conidial suspension ($10^5$ conidia per milliliter) were placed on 150 V-8 juice agar plates and exposed to ultraviolet (UV) irradiation for 80 min. Irradiation was provided by two adjacent (7 cm apart) G-E Germicidal Lamps (G36T6, General Electric Co.). Any U.V. lamp or suitable source of U.V. radiation may be used. The plates, with the lids removed, were irradiated at a distance of 25 cm from the agar surface to the lamps. The irradiated plates were covered and incubated at 25°-2° C. under fluorescent light. Ten colonies developed from $1.5 \times 10^7$ conidia irradiated. The colonies isolated and grown on V-8 juice agat were designated as T-1-R1 to T-1-R10 and will hereafter be referred to as R1 to R10.

Since no recognizable markers were available with strain T-1 of *T. viride*, tolerance to fungicides in the methyl benzimidazole carbamate group was used as the criterion to distinguish mutants from the wild strain. The fungicides benomyl, thiabendazole, and thiophanate methyl, as described above, were suspended in sterile distilled water and added to potato-dextrose broth (PDB) (40 per 250-ml Erlenmeyer flask) at 0, 50, and 100 $\mu$g active ingredient (a.i)/ml. Disks (5 mm diameter) of 7-day old colonies of T-1 and of the 10 biotypes were transferred to flasks. Dry weights of mycelial mats of flask cultures were determined after 1 and 3 weeks of incubation.

Comparative toxicity of benomyl (added to V-8 juice agar at 0, 25, 50, and 100 $\mu$g a.i./ml) on spore germination of T-1 and of the 10 biotypes was determined. One-ml aliquots of aqueous conidial suspensions ($1 \times 10^4$ conidia/ml) were pipetted onto the surface of V-8 juice agar containing benomyl in petri plates and incubated at 25°±2° C. under fluorescent light. After 24, 36, and 48 hours, selected areas in the plates were stained with lacto-fuchsin and germinated and nongerminated conidia counted. Germinability readings were based on 100 conidia per replication, five replications per treatment, and the data were expressed as percent inhibition of germination.

In the PDB-benomyl test, growth of the wild strain T-1 was completely inhibited at 50 and 100 μg of benomyl per milliliter. Four of the 10 biotypes (R1, R2, R3, R4) tested in this experiment grew as well at 50 μg of benomyl per milliliter of PDB as in the untreated control; and the growth of the other six (R5 to R10) was reduced by about 50% at those concentrations of benomyl. Growth of T-1 and of the 10 biotypes in the PDB-thiophanate methyl test was similar to that observed in the PDB-benomyl test, except that thiophanante methyl was slightly less toxic to T-1 than benomyl. In the PDB-thiabendazole (PDB-TBZ) test, growth of the wild strain T-1 was completely inhibited at 50 and 100 μg of TBZ per milliliter. TBZ, however, was more inhibitory to the UV-induced biotypes than benomyl. Growth of three biotypes (R2, R3, R5) was inhibited by about 25 and 40% at both concentrations of TBZ after 1 and 3 weeks, respectively. Growth of the other biotypes was inhibited by almost 70%.

Benomyl prevented from 85 to 100% of conidia of the wild strain T-1 from germinating at 25, 50, and 100 μg a.i./ml. In contrast, benomyl prevented only less than 10% of conidia of R1 and R2 from germinating, even at 100 μg/ml. Conidia of R3 and R4 germinated 100% even at 100 μg a.i./ml of benomyl. Benomyl prevented approximately 45–50% of the conidia of R9 and those of the remaining biotypes (R5, R6, R7, R8, R10) from germinating.

The gliotoxin fermentation medium described in Am. Appl. Biol. 32, 214–220, 1945, was used to determine the effect of culture medium pH on growth. The best growth of T-1 and of all the biotypes was obtained at pH 3.5.

Antagonistic activities of strain T-1 and of the ten biotypes against eight soilborne plant pathogens were determined in vitro on potato dextrose agar (PDA) (22 ml/plate). The eight soilborne pathogens are *Fusarium oxysporum* f.sp. *melonis*, *F. solani* f. sp. *phaseoli*, *Phytophthora capsici*, *Pythium ultimum*, *Sclerotium cepivorum*, *S. rolfsii*, *Rhizoctonia solani*, and *Verticillium dahliae*. Disks (4 mm diameter) from the edge of 4-day old colonies of the Trichoderma cultures and of 7-day old colonies of the pathogens, all grown on PDA, were paired on the medium, on opposite sides of 10 × 1.5 cm petri plates. The antagonist disks were placed 3 cm from those of the pathogens. Isolates of *P. capsici*, *R. solani*, *S. cepivorum*, and *V. dahliae* were placed on the agar 48 hours before the antagonists. All other combinations were done simultaneously. The cultures were incubated at 25° C. under continuous fluorescent light of the same intensity as before and examined for antagonistic zones after 7 days.

The wild strain T-1 and biotypes R5 through R10 did not produce zones of inhibition against any of the pathogens. Biotypes R1 and R2 produced zones of inhibition against *F. oxysporum* f. sp. *melonis* only. Biotypes R3 and R4 were the only ones that exhibited a broader spectrum of in vitro antagonism, producing inhibitory zones when paired with five of the eight pathogens, *F. oxysporum* f. sp. *melonis*, *F. solani* f. sp. *phaseoli*, *P. capsici*, *S. cepivorum*, and *V. dahliae*. None of the biotypes exhibited antagonism against *P. ultimum*, *R. solani*, and *S. rolfsii*.

The ability of T-1 and the ten biotypes to suppress disease was also determined. Conidia of T-1 and of the 10 UV-induced biotypes were harvested from 8-day old cultures growing on V-8 juice agar by rubbing, with a cotton-tipped applicator, sporulating surfaces to which 2 ml of 4% methyl cellulose (MC) solution had been added. Suspensions of conidia were counted in a hemacytometer and adjusted to contain $2.5 \times 10^9$ conidia per milliliter, of which 98% germinated. One milliliter of the spore-MC suspensions was applied to 20 g of Perfected Freezer pea seed (*Pisum sativum* L.) and the seeds were allowed to dry. The 1 ml conidial suspension theoretically added $1.25 \times 10^8$ conidia/g of seed. Treated and untreated seeds and seeds treated with thiram, a known fungicide, were planted in 11 cm diameter plastic pots (10 seeds per pot) containing a sandy loam naturally infested with *Pythium ultimum* Trow. The pots were incubated at 18° C. and plant stands were determined 11 and 25 days after planting.

In a second test, *Sclerotium rolfsii* Sacc. sclerotia, produced on PDA, were added to a sandy loam at 50 sclerotia/100 g of soil and mixed thoroughly. The soil was divided into 10-kg portions to receive treatments. Aqueous suspensions of conidia from V-8 Juice agar plates of T-1 and of the 10 UV-induced biotypes were added to *S. rolfsii*-infested soil to provide $6 \times 10^5$ colony forming units (cfu) per gram of soil. One week after treatment, the soil portions were subdivided into 1-kg batches and these were placed in 11 cm diameter plastic pots. Untreated bean seed (*Phaseolus vulgaris* L.) cv. Blue Lake 274 were planted at 10 seeds per pot and these were incubated in a greenhouse compartment at $27° \pm 2°$ C. The plants were harvested and evaluated for disease 1½ and 5 weeks after planting.

Conidia of T-1 and the biotypes R1, R3, R4, R5, R6, R8, and R10, added to Perfected Freezer pea seed at equal population densities, resulted in significantly less preemergence damping-off than that obtained in an untreated control or in a methyl cellulose control at 11 days post-planting. Twenty five days after planting, T-1 and all biotype seed treatments, except R2, significantly suppressed seed rot and damping-off. Conidia of R1 at 11 days, and those of R1 and R4 at 25 days after planting resulted in significantly better stand than that obtained with T-1 and equal to that obtained with thiram.

In the *S. rolfsii* test, aqueous suspensions of conidia of T-1, R5, and R6, all added at $6 \times 10^5$ cfu per gram of soil, significantly suppressed bean damping-off and blight as determined at the 1½ week postplant examination. None of the UV-induced biotypes was significantly better at 1½ weeks than the wild strain. Five weeks after planting, only biotypes R5 and R6 significantly suppressed disease, compared to the control; and disease suppression by R5 and R6 was statistically significant from that brought about by the wild strain T-1 and not significant from an uninfested control. Biotype R9 was ineffective in controlling *S. rolfsii* in this test.

The efficacy of biotype R9 against wilt of chrysanthemum caused by *Fusarium oxysporum* f. sp. *chrysanthemi* was compared with that of twenty one other fungi. Biotype R9 gave excellent protection against the disease. In fact, R9 provided control equal to that provided by the commercially established integrated control system involving the use of benomyl, nitrate nitrogen and high pH. Biotype R9 also produces an abundance of conidia and chlamydospores on inexpensive liquid and solid media, a particularly valuable consideration for large scale production. The other biotypes, R1 to R8 and R10, did not provide any protection against the wilt of chrysanthemum caused by *Fusarium oxysporum* f. sp. *chrysanthemi*.

Although the new biocontrol agent of this invention, *Trichoderma viride* biotype T-1-R9, has been found to be effective only against the wilt of chrysanthemum caused by *Fusarium oxysporum* f. sp. chrysanthemi, further investigation may prove it to be effective against other diseases caused by other Fusarium species.

In controlling the wilt of chrysanthemum caused by *Fusarium oxysporum* f. sp. *chrysanthemi* conidia of biotype T-1-R9 are added to the soil at a minimum concentration of $6 \times 10^5$ conidia per gram of soil.

I claim:

1. A biologically pure culture of the fungus *Trichoderma viride* designated as T-1-R9.

2. A biocontrol agent for controlling and suppressing Fusarium wilt of chrysanthemum caused by *Fusarium oxysporum* f. sp. *chrysanthemi* comprising a biologically pure culture of *Trichoderma viride* biotype T-1-R9.

* * * * *